(12) United States Patent
Nicholas et al.

(10) Patent No.: US 8,480,703 B2
(45) Date of Patent: Jul. 9, 2013

(54) SURGICAL DEVICE

(75) Inventors: David A. Nicholas, Trumbull, CT (US);
David A. Zeichner, Oxford, CT (US);
Donald Malinouskas, Monroe, CT (US)

(73) Assignee: Covidien LP, Mansfield, MA (US)

( * ) Notice: Subject to any disclaimer, the term of this patent is extended or adjusted under 35 U.S.C. 154(b) by 108 days.

(21) Appl. No.: 13/209,509

(22) Filed: Aug. 15, 2011

(65) Prior Publication Data

US 2012/0130420 A1    May 24, 2012

Related U.S. Application Data

(60) Provisional application No. 61/415,430, filed on Nov. 19, 2010.

(51) Int. Cl.
*A61B 17/00*    (2006.01)

(52) U.S. Cl.
USPC ......... 606/205; 606/142; 606/167; 227/175.1

(58) Field of Classification Search
None
See application file for complete search history.

(56) References Cited

U.S. PATENT DOCUMENTS

| 5,478,003 | A * | 12/1995 | Green et al. ............... 227/176.1 |
| 5,662,662 | A * | 9/1997 | Bishop et al. ................. 606/143 |
| 5,741,285 | A | 4/1998 | McBrayer et al. |
| 5,827,323 | A | 10/1998 | Klieman et al. |
| 7,540,867 | B2 * | 6/2009 | Jinno et al. ........................ 606/1 |
| 7,605,559 | B2 | 10/2009 | Messerly et al. |
| 7,875,029 | B1 | 1/2011 | Hausen |
| 2005/0222587 | A1 * | 10/2005 | Jinno et al. ..................... 606/130 |
| 2006/0190034 | A1 | 8/2006 | Nishizawa et al. |
| 2006/0259073 | A1 | 11/2006 | Miyamoto et al. |
| 2007/0208375 | A1 | 9/2007 | Nishizawa et al. |
| 2009/0101692 | A1 | 4/2009 | Whitman et al. |
| 2009/0112230 | A1 * | 4/2009 | Jinno ............................. 606/130 |
| 2010/0152533 | A1 | 6/2010 | Mark |
| 2010/0152614 | A1 | 6/2010 | Mark |
| 2011/0062211 | A1 * | 3/2011 | Ross et al. ................. 227/175.1 |
| 2011/0106078 | A1 * | 5/2011 | Mueller .......................... 606/52 |

* cited by examiner

*Primary Examiner* — Corrine M McDermott
*Assistant Examiner* — Todd J Scherbel (57) ABSTRACT

A surgical device includes a shaft portion coupled to a handle, the handle defining a longitudinal axis. The surgical device also includes a first driver configured to actuate a rotational movement via a first drive shaft and a second driver configured to actuate an articulation movement via a second drive shaft. The surgical device also includes a controller having a first dial and a second dial, the first dial actuated by the first driver and the second dial actuated by the second driver, the second dial positioned within the first dial.

15 Claims, 5 Drawing Sheets

SURGICAL DEVICE

CROSS REFERENCE TO RELATED APPLICATION

The present application claims the benefit of and priority to U.S. Provisional Application Ser. No. 61/415,430 filed on Nov. 19, 2010, the entire contents of which are incorporated herein by reference.

BACKGROUND

1. Technical Field

The present disclosure relates to a surgical device and, more particularly, to a powered rotating and/or articulating surgical device having a controller supported on a handle having a cab-forward configuration.

2. Background of Related Art

One type of surgical device is a linear clamping, cutting, and stapling device. Such a device may be employed in a surgical procedure to, for example, resect a cancerous or anomalous tissue from a gastro-intestinal tract. A conventional linear clamping, cutting, and stapling device may include a pistol grip-styled structure having an elongated shaft and distal portion. The distal portion may include a scissors-styled gripping element. In this device, one member of the scissors-styled gripping element, such as the anvil portion, moves or pivots relative to the overall structure, whereas the other member of the scissors-styled gripping element remains fixed relative to the overall structure. The actuation of this gripping element may be controlled by a trigger maintained in or on the handle.

In addition to the scissors-styled gripping element, the distal portion of the stapling device may also include a stapling mechanism. The fixed member of the gripping element may include a staple cartridge receiving region and a mechanism for driving staples up, through clamped tissue, and against an anvil portion, thereby sealing the previously opened end of the tissue. The gripping elements may be integrally formed with the shaft or may be detachable such that various gripping, scissoring, and/or stapling elements may be interchangeable.

It may be necessary for a surgeon to move the opposing gripping elements between various angles in order to position the desired tissue between the opposing gripping elements. Thus, a need exists for improvements in the maneuverability of clamping, cutting, and stapling devices.

SUMMARY

The present disclosure relates to powered rotating and/or articulating surgical devices having a controller supported on a handle having a cab-forward configuration.

According to an aspect of the present disclosure, a surgical device is provided including a handle configured to be held by a hand of an operator; a shaft portion coupled to the handle, the shaft portion defining a shaft longitudinal axis; an end effector supported on a distal end of the shaft portion so as to rotate and pivot relative to the shaft portion; a first drive shaft extending through the shaft portion and operatively connected to the end effector to effectuate a rotation of the end effector about the shaft longitudinal axis of the shaft portion; a second drive shaft extending through the shaft portion and operatively connected to the end effector to effectuate a pivoting of the end effector relative to the shaft longitudinal axis of the shaft portion; and a controller supported on the handle so as to be actuated by a thumb of the hand of the operator holding the handle. The controller includes a first rotatable member; and a second rotatable member. The first rotatable member is configured to rotate the first drive shaft in one of a first direction and a second direction upon a corresponding first direction and second direction rotation thereof to effectuate a corresponding first direction rotation and second direction rotation of the end effector relative to the shaft portion. The second rotatable member is configured to rotate the second drive shaft in one of a first direction and a second direction upon a corresponding first direction and second direction rotation thereof to effectuate a corresponding first direction pivoting and second direction pivoting of the end effector relative to the shaft portion.

The first rotatable member may define an axis of rotation and the second rotatable member may define an axis of rotation, wherein the axis of rotation of the second rotatable member may be orthogonally oriented with respect to the axis of rotation of the first rotatable member.

The first rotatable member may define an axis of rotation and the second rotatable member may define an axis of rotation, and wherein the axis of rotation of the second rotatable member may be substantially parallel with respect to the axis of rotation of the first rotatable member.

The axis of rotation of the second rotatable member may be concentric with respect to the axis of rotation of the first rotatable member.

The first rotatable member and the second rotatable member may be nested within one another.

The controller may include a first Hall-Effect switch associated with the first rotatable member for effectuating the rotation of the first drive shaft; and a second Hall-Effect switch associated with the second rotatable member for effectuating the rotation of the second drive shaft.

The surgical device may further include a feedback mechanism for providing at least one of tactile and audible feedback relating to the rotational movement and the pivoting movement of the end effector. The feedback mechanism may include a leaf spring engaged with teeth provided on each of the first rotatable member and the second rotatable member.

The end effector may be pivotably connected to the distal end of the shaft portion so as to pivot in a single plane about a pivot axis extending substantially orthogonal to the shaft longitudinal axis.

According to an aspect of the present disclosure, a rate of rotation of the end effector may be commensurate in scope with a rate of rotation of the first rotatable member, and a rate of pivoting of the end effector may be commensurate in scope with a rate of rotation of the second rotatable member. A relatively slow rate of rotation of the first rotatable member may result in a rate of rotation of the end effector having a ratio of approximately 1:1. A relatively slow rate of rotation of the second rotatable member may result in a rate of pivoting of the end effector having a ratio of approximately 1:1. A relatively fast rate of rotation of the first rotatable member may result in a rate of rotation of the end effector having a ratio greater that 1:1. A relatively fast rate of rotation of the second rotatable member may result in a rate of pivoting of the end effector having a ratio greater than 1:1.

The handle may include an upper portion supporting the shaft portion; and an intermediate portion extending from the upper portion, wherein the intermediate portion may define a longitudinal axis, and wherein the longitudinal axis of the intermediate portion may be oriented at an angle of approximately 30° relative to the shaft longitudinal axis.

The end effector may include a jaw portion.

According to a further aspect of the present disclosure, a surgical device is provided and includes a handle configured to be held by a hand of an operator in a pistol-grip fashion; a shaft portion extending from the handle, the shaft portion defining a shaft longitudinal axis; an end effector supported on a distal end of the shaft portion, the end effector being able to rotate and pivot relative to the shaft portion; and a controller supported on the handle so as to be actuated by a thumb of the hand of the operator holding the handle with a single hand. The controller includes a first rotatable member; and a second rotatable member. The first rotatable member is configured to rotate in one of a first direction and a second direction to effectuate a corresponding first direction rotation and second direction rotation of the end effector relative to the shaft portion. The second rotatable member is configured to rotate in one of a first direction and a second direction to effectuate a corresponding first direction pivoting and second direction pivoting of the end effector relative to the shaft portion.

The first rotatable member may define an axis of rotation and the second rotatable member may define an axis of rotation. The axis of rotation of the second rotatable member may be orthogonally oriented with respect to the axis of rotation of the first rotatable member.

The controller may include a first Hall-Effect switch associated with the first rotatable member for effectuating the rotation of the end effector; and a second Hall-Effect switch associated with the second rotatable member for effectuating the rotation of the end effector.

The end effector may be pivotably connected to the distal end of the shaft portion so as to pivot in a singe plane about a pivot axis extending substantially orthogonal to the shaft longitudinal axis.

It is contemplated that a rate of rotation of the end effector may be commensurate in scope with a rate of rotation of the first rotatable member. A rate of pivoting of the end effector may be commensurate in scope with a rate of rotation of the second rotatable member. Accordingly, a relatively slow rate of rotation of the first rotatable member may result in a rate of rotation of the end effector having a ratio of approximately 1:1. A relatively slow rate of rotation of the second rotatable member may result in a rate of pivoting of the end effector having a ratio of approximately 1:1. A relatively fast rate of rotation of the first rotatable member may result in a rate of rotation of the end effector having a ratio greater that 1:1. A relatively fast rate of rotation of the second rotatable member may result in a rate of pivoting of the end effector having a ratio greater than 1:1.

According to another aspect of the present disclosure, a method of operating a surgical device is provided. The method includes the steps of providing a surgical device including a handle configured to be held by a hand of an operator in a pistol-grip fashion; a shaft portion extending from the handle, the shaft portion defining a shaft longitudinal axis; an end effector supported on a distal end of the shaft portion, the end effector being able to rotate and pivot relative to the shaft portion; and a controller supported on the handle so as to be actuated by a thumb of the hand of the operator holding the handle with a single hand. The controller includes a first rotatable member; and a second rotatable member. The first rotatable member is configured to rotate in one of a first direction and a second direction to effectuate a corresponding first direction rotation and second direction rotation of the end effector relative to the shaft portion. The second rotatable member is configured to rotate in one of a first direction and a second direction to effectuate a corresponding first direction pivoting and second direction pivoting of the end effector relative to the shaft portion. The method further includes the step of performing at least one of rotating the first rotatable member to effectuate a rotation of the end effector relative to the shaft portion; and rotating the second rotatable member to effectuate a pivoting of the end effector relative to the shaft portion.

According to an aspect of the present disclosure, a surgical device is provided and includes a shaft portion coupled to a handle, the handle defining a longitudinal axis; a first driver configured to actuate a rotational movement via a first drive shaft; a second driver configured to actuate an articulation movement via a second drive shaft; and a controller having a first dial and a second dial. The first dial is configured to actuate the first driver and the second dial is configured to actuate the second driver. The second dial is positioned within the first dial.

The second dial may be oriented perpendicularly with respect to the first dial. The first dial and the second dial may be are operable concurrently.

The surgical device may further include a first Hall-Effect switch for effectuating the rotational movement and a second Hall-Effect switch for effectuating the articulation movement.

The surgical device may further include a feedback mechanism for providing feedback relating to the rotational movement and the articulation movement actuated by a user. The feedback mechanism may include a leaf spring in contact with at least one of the first dial and the second dial.

According to another aspect of the present disclosure, a method of operating a surgical device is provided. The method includes the steps of providing a surgical device including a shaft portion interconnecting an end effector and a handle, the shaft defining a longitudinal axis; a first driver configured to actuate a rotational movement via a first drive shaft; a second driver configured to actuate an articulation movement via a second drive shaft; and a controller having a first dial and a second dial. The first dial is configured to actuate the first driver and the second dial is configured to actuate the second driver. The second dial is positioned within the first dial. The method further includes the steps of rotating the first dial to effectuate a rotation of the end effector relative to the shaft; and/or rotating the second dial to effectuate an articulation of the end effector relative to the shaft.

According to a further aspect of the present disclosure, a surgical device is provided and includes a handle; a shaft portion extending from the handle, the shaft defining a longitudinal axis; an end effector supported on a distal end of the shaft portion; a first driver configured to effectuate a rotation of the end effector relative to the shaft via a first drive shaft; a second driver configured to effectuate actuate an articulation of the end effector relative to the shaft via a second drive shaft; and a controller supported on the handle, the controller having a first dial and a second dial positioned within the first dial. The first dial is configured to actuate the first driver and effectuate a rotation of the end effector relative to the shaft upon a rotation thereof. The second dial is configured to actuate the second driver and effectuate actuate an articulation of the end effector relative to the shaft via a second drive shaft.

The second dial may be oriented perpendicularly with respect to the first dial.

The surgical device may further include a first Hall-Effect switch associated with the first dial and a second Hall-Effect switch associated with the second dial.

The surgical device may further include a feedback mechanism associated with each of the first dial and the second dial for providing feedback relating to the rotation and articulation transmitted to the end effector. The feedback mechanism may include a leaf spring in contact with each of the first dial and the second dial.

The surgical device may be configured such that rotation of the first dial effectuates a rotation of the end effector relative to the shaft; and rotation of the second dial effectuates an articulation of the end effector relative to the shaft.

Rotation of the first dial in a first direction may effectuate a rotation of the end effector in a first direction and rotation of the first dial in a second direction may effectuate a rotation of the end effector in a second direction.

Rotation of the second dial in a first direction may effectuate an articulation of the end effector in a first direction and rotation of the second dial in a second direction may effectuate an articulation of the end effector in a second direction.

The handle may have a cab-forward configuration.

BRIEF DESCRIPTION OF THE DRAWINGS

Various embodiments of the presently disclosed surgical instrument are described hereinbelow with references to the drawings, wherein.

DETAILED DESCRIPTION OF THE EMBODIMENTS

In the figures and in the description that follows, in which like reference numerals identify similar or identical elements, the term "proximal" will refer to the end of the apparatus which is closest to the operator during use, while the term "distal" will refer to the end which is farthest from the operator, as is traditional.

Figure 1A:
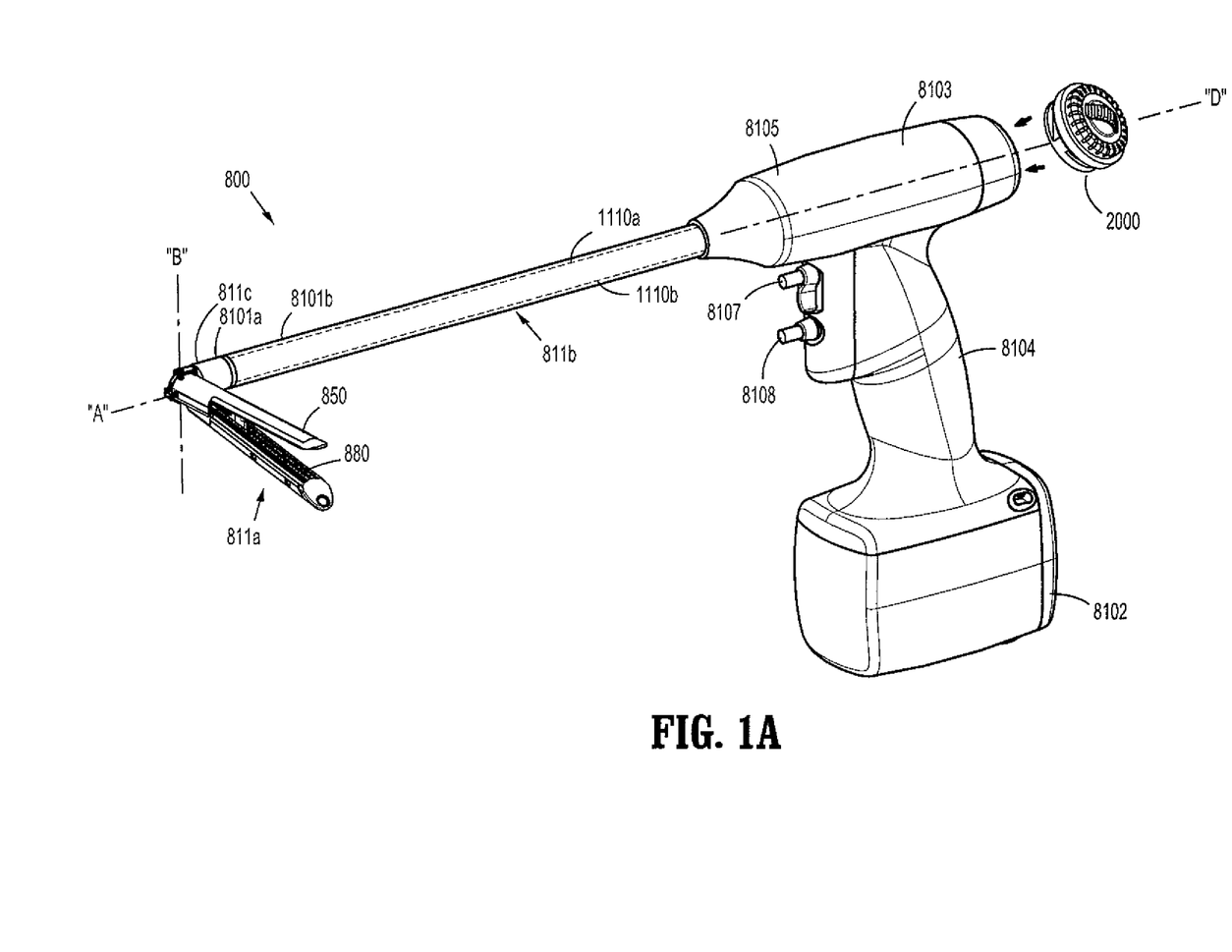
FIG. 1A is a perspective view of a surgical device having a controller, in accordance with the present disclosure.
Figure 1B:
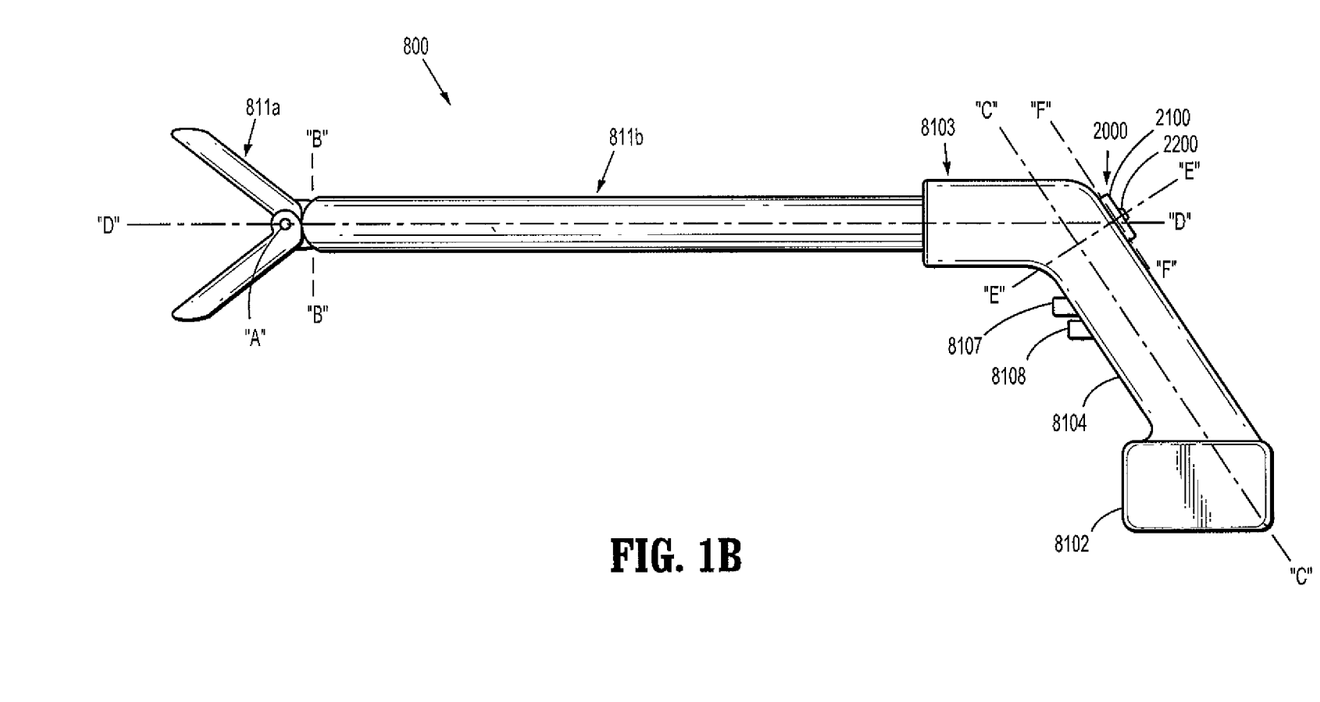
FIG. 1B is a schematic side elevational view of the surgical device of FIG. 1A.

Referring to FIGS. 1A and 1B, a perspective view of a surgical device having a controller, in accordance with the present disclosure is presented.

In FIGS. 1A and 1B, there is shown a surgical device 800 that may be configured to stand alone, e.g., that includes various motors, drive shafts, control systems, etc., in an integral arrangement such that attachment to a separate electromechanical surgical system may be eliminated. Such an arrangement may include the advantage that surgical device 800 may not be connected prior to use to a separately-disposed drive system. Surgical device 800 may be configured so as to be particularly well-suited for insertion into the body of a patient, e.g., via a cannula (not shown). Surgical device 800 may be a clamping, cutting, and stapling device.

Surgical device 800 may include an end effector or jaw portion 811a that may be pivotably coupled to a shaft portion 811b by a hinge portion 811c. As seen in FIGS. 1A and 1B, shaft portion 811b defines a longitudinal axis "D". Jaw portion 811a may include a first jaw 850 having a distal end and a proximal end, and a second jaw 880 having a distal end and a proximal end. First jaw 850 and second jaw 880 may be pivotably coupled relative to each other at or near their respective proximal ends. As shown in FIGS. 1A and 1B, first jaw 850 and second jaw 880 may be pivotable relative to each other about pivot axis "A". In this arrangement, the jaws may be configured such that, upon opening and closing of first jaw 850 relative to second jaw 880 and at points in the movement of first jaw 850 relative to second jaw 880, both first jaw 850 and second jaw 880, e.g., their longitudinal axes remain within a plane. It should be understood, however, that surgical device 800 may instead be configured such that first jaw 850 and second jaw 880 may be pivotable relative to each other about a pivot axis that may be oriented differently from that shown in FIGS. 1A and 1B.

As mentioned above, jaw portion 811a may be pivotably coupled to shaft portion 811b by hinge portion 811c. Specifically, jaw portion 811a may be pivotable relative to shaft portion 811b about a pivot axis "B", which may be positioned at any location on or between jaw portion 811a and shaft portion 811b, and at any circumferential location relative to jaw portion 811a and shaft portion 811b. In the example embodiment shown, pivot axis B may be oriented vertically, and within the page. In this arrangement, jaw portion 811a and shaft portion 811b may be configured such that, upon articulation of jaw portion 811a relative to shaft portion 811b and at any point in the movement of jaw portion 811a relative to shaft portion 811b, jaw portion 811a and shaft portion 811b remain within a plane that may be perpendicular to pivot axis "B". It should be recognized that, in other example embodiments, pivot axis "B" may have a different orientation, so as to enable jaw portion 811a to pivot within a different plane. Jaw portion 811a may be pivotable to and between any angles relative to shaft portion 811b, such that jaw portion 811a may be selectively positioned as desired during use.

Furthermore, surgical device 800 may provide rotation of various components about a longitudinal axis of surgical device 800. For example, in various embodiments, jaw portion 811a and/or shaft portion 811b may be rotatable relative to a handle 8103 (described in additional detail below). Handle 8103 is attached to a proximal end of shaft portion 811b and may be rotatable along the longitudinal axis "D". Shaft portion 811b defines a distal portion 8101a, to which jaw portion 811a is connected, and a proximal portion 8101b, which is connected to handle 8103.

Generally, handle 8103 may be grasped by an operator to operate surgical device 800. Handle 8103 includes a proximal or base portion 8102, an intermediate portion 8104 extending from base portion 8102 and which may include several finger-actuated control buttons 8107, 8108, and a distal or upper portion 8105 that is connected to shaft portion 811b.

Reference may be made to U.S. Patent Publication 2009/0101692, the entire content of which is incorporated herein by reference for a more detailed discussion of the construction and operation of jaw portion 811a and of surgical device 800.

In accordance with the present disclosure, handle 8103 is designed and constructed so as to provide improved ergonomics and increased comfort to an operator. In this regard, intermediate portion 8104 of handle 8103 may define a longitudinal axis "C" extending at an angle from longitudinal axis "D" defined by shaft portion 811b. In particular, as seen in FIG. 1B, longitudinal axis "C" of intermediate portion 8104 of handle 8103 defines an angle of inclination of approximately 30° relative to longitudinal axis "D" defined by shaft portion 811b.

FIGS. 1A and 1B also illustrates a controller 2000, which will be described in more detail below with reference to FIGS. 2-4. Controller 2000 functions to effectuate pivoting of jaw portion 811a relative to shaft portion 811b and to effectuate rotation, about longitudinal axis "D", of jaw portion 811a relative to shaft portion 811b or of shaft portion 811b relative to handle 8103.

Controller 2000 may include a first rotatable member 2100 (in the form of a wheel or dial) and a second rotatable member 2200 (in the form of a wheel or dial). First rotatable member 2100 may be in operable communication with second rotatable member 2200 and may both be supported within a housing 2300. First rotatable member 2100 may be used to control rotational movement of one or more components of surgical device 800, whereas second rotatable member 2200 may be used to control longitudinal/articulation/pivoting movement of the one or more components of surgical device 800. For example, first rotatable member 2100 may be used to pivot jaw portion 811a about pivot axis "B", whereas second rotatable member 2200 may be used to pivot jaw portion 811a about the longitudinal axis "D". Thus, controller 2000 of surgical device 800 may act as a rotation/articulation/pivot controller.

In an example embodiment, controller 2000 may be a dual wheel/dial configuration that may be suitably positioned, e.g., on a top or rear surface of handle 8103, and sized so as to be actuatable by an operator's thumb when the operator is holding handle 8103 in a pistol grip fashion. As discussed above, it is contemplated that handle 8103 may be designed and configured to provide more comfortable ergonomics for an operator when controller 2000 is located on a rear surface of upper portion 8105 of handle 8103. It is contemplated, in an embodiment, that controller 2000 is disposed on handle 8103 so as to be aligned with the longitudinal axis "D" of shaft portion 811b. As seen in FIGS. 3A and 3B, first rotatable member 2100 defines an axis of rotation "E" that is substantially parallel with or is angled at an acute angle relative to the longitudinal axis "D" defined by shaft portion 811b. Additionally, as seen in FIGS. 3A and 3B, second rotatable member 2200 defines an axis of rotation "F" that is substantially orthogonal to axis of rotation "E" of first rotatable member 2100. It is further contemplated that axis of rotation "E" of first rotatable member 2100 and axis of rotation of "F" of second rotatable member 2200 intersect one another.

While a dual dial mechanism is shown for controller 2000, one skilled in the art may contemplate a controller including a plurality of different dials having a plurality of different shapes and sizes and interconnected in a plurality of configurations or orientations on any portion of surgical device 800. For example, in one embodiment controller 2000 may include at least a pair of dials, each defining an axis of rotation, wherein the axes of rotation are substantially parallel to one another. In another embodiment, controller 2000 may include at least a pair of concentric dials sharing a common axis of rotation. It is further contemplated that controller 2000 may include a ball supported in handle 8103 so as to rotate in any axis. In accordance with another embodiment of the present disclosure, the first rotatable member 2100 and the second rotatable member 2200 are nested within one another.

In use, rotation of first rotatable member 2100 in a clockwise direction may effectuate rotation of jaw portion 811a in a clockwise direction relative to handle 8103, whereas rotation of first rotatable member 2100 in a counter-clockwise direction may effectuate rotation of jaw portion 811a in a counter-clockwise direction relative to handle 8103. Similarly, rotation of second rotatable member 2200 in a clockwise direction may effectuate pivoting of jaw portion 811a in a first direction relative to handle 8103, whereas rotation of second rotatable member 2200 in a counter-clockwise direction may effectuate pivoting of jaw portion 811a in a second direction relative to handle 8103, where the second direction is opposite the first direction.

In accordance with the present disclosure, it is contemplated that the speed at which first rotatable member 2100 is rotated by the user or operator may control the speed of rotation of jaw portion 811a, whereas the speed at which second rotatable member 2200 is rotated by the user may control the speed of pivoting of jaw portion 811a. It is further contemplated that an incremental rotation of first rotatable member 2100 results in incremental rotation of jaw portion 811a, and incremental rotation of second rotatable member 2200 results in incremental pivoting of jaw portion 811a. Stated differently, the speed or rotation of jaw portion 811a is commensurate to the speed of rotation of first rotatable member 2100, and the speed of pivoting of jaw portion 811a is commensurate to the speed of rotation of second rotatable member 2200. In this manner, if an operator slowly rotates first and/or second rotatable member 2100, 2200, jaw portion 811a is slowly rotated and/or pivoted, and if an operator quickly rotates first and/or second rotatable member 2100, 2200, jaw portion 811a is quickly rotated and/or pivoted.

It is further contemplated that the rate at which first and/or second rotatable member 2100, 2200 is/are rotated by an operator will vary or determine a degree of rotation and/or pivoting of jaw portion 811a. For example, if an operator slowly rotates first and/or second rotatable member 2100, 2200, jaw portion 811a will rotate and/or pivot at a selected first rate (e.g., at a ratio of approximately 1:1). However, if an operator quickly rotates first and/or second rotatable member 2100, 2200, jaw portion 811a will rotate and/or pivot at a selected second rate, faster that the first rate, (e.g., at a ratio of approximately 2:1 or 3:1 or any desired ratio greater than 1:1).

Figure 2:
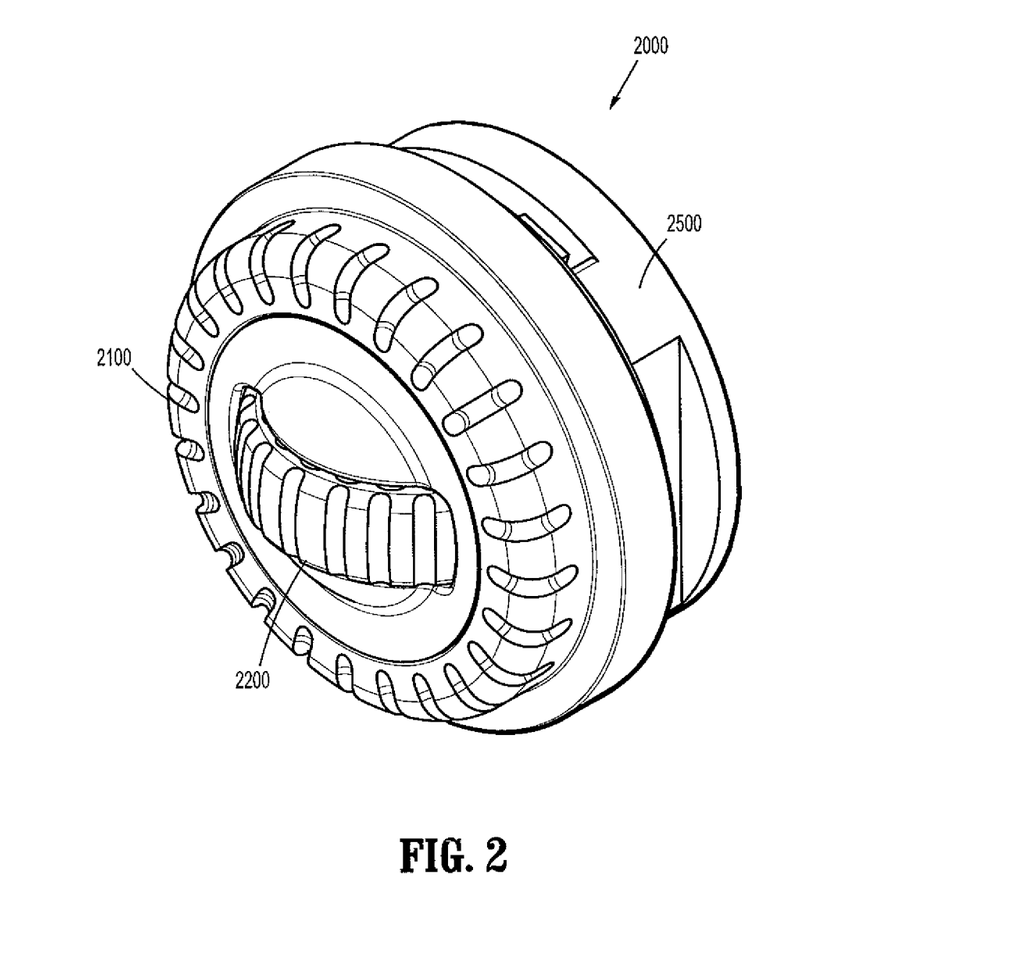
FIG. 2 is a perspective view of the controller, in accordance with the present disclosure.
Figure 3A:
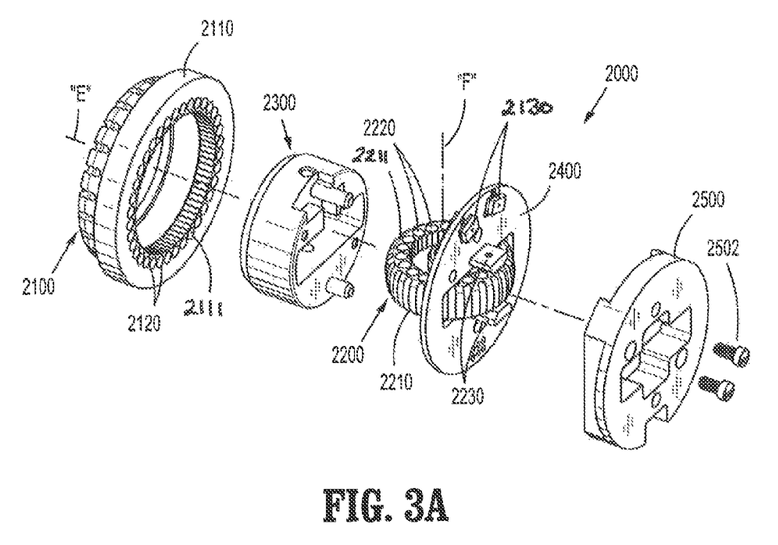
FIGS. 3A and 3B are exploded, perspective views of the controller, in accordance with the present disclosure.
Figure 3B:
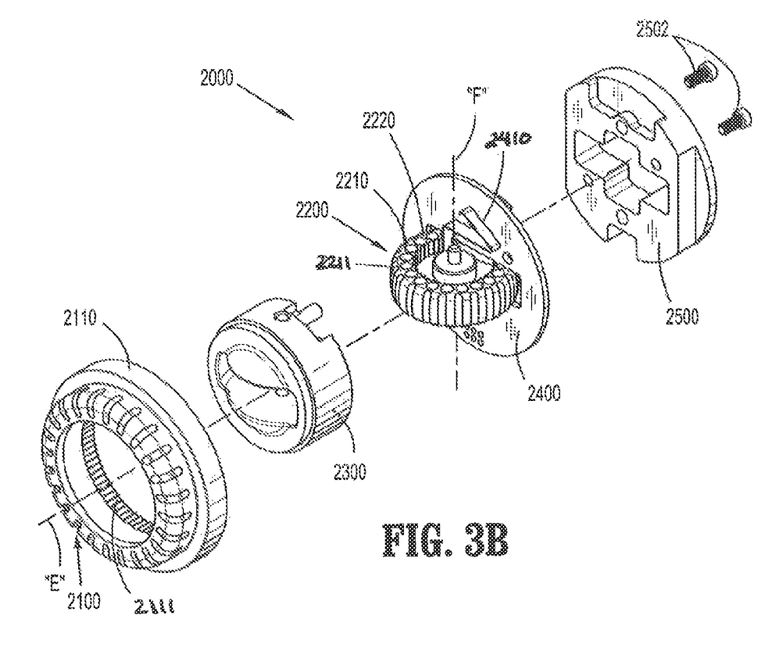

Referring to FIGS. 3A and 3B, exploded, perspective views of controller 2000 of FIG. 2, in accordance with the present disclosure are presented.

As seen in FIGS. 3A and 3B, controller 2000 includes the first rotatable member 2100 which is in the form of a rotation wheel 2110 supporting a plurality of magnets 2120. The plurality of magnets 2120 may be supported in/on rotation wheel 2110 with alternating north and south poles around a perimeter of rotation wheel 2110. First rotatable member 2100 of controller 2000 is rotatably supported on or about support housing 2300 and defines an axis of rotation "E".

Controller 2000 further includes the second rotatable member 2200 which is in the form of a rotation wheel 2210 supporting a plurality of magnets 2220. The plurality of magnets 2220 may be supported in/on rotation wheel 2210 with alternating north and south poles around a perimeter of rotation wheel 2210. Rotation wheel 2210 is rotatably supported in/on support housing 2300 and defines an axis of rotation "F". Controller 2000 further includes a base member 2400 operatively associated with rotation wheels 2110 and 2210.

Base member 2400 supports a plurality of Hall-Effect switches thereon. In particular, base member 2400 supports a first Hall-Effect switch 2130 thereon such that first Hall-Effect switch 2130 is in magnetic registration with the plurality of magnets 2120 of rotation wheel 2110. Base member 2400 also supports a second Hall-Effect switch 2230 thereon such that second Hall-Effect switch 2230 is in magnetic registration with the plurality of magnets 2220 of rotation wheel 2210. While Hall-Effect switches 2130 and 2230 are shown and described, it is within the scope of the present disclosure that controller 2000 may be provided with optical sensors, illumination members in registration with the optical sensors, and the like to accomplish the tasks and objectives of the Hall-Effect switches.

Controller 2000 includes a backing member 2500 that is configured to support the support housing 2300 and base member 2400 via fastening members 2502. Controller 2000 further includes a ratchet member 2410, in the form of a half-spring, supported on base member 2400. Ratchet member 2410 is operatively engaged with a set of ratchet teeth 2111 formed on first rotatable member 2100 and a set of ratchet teeth 2211 formed on second rotatable member 2200. Ratchet member 2410 may provide a degree of tactile and/or audible feedback to the user as either first and/or second rotatable members 2100 and/or 2200 is/are rotated in the form of a clicking sound. For example, a series of nubs or ribs may be provided on a surface of rotation members 2100, 2200 and at least one nub may be provided on a surface in juxtaposed relation to the nubs/ribs of rotatable members 2100, 2200. It is further contemplated that the audible sounds may be synthesized electronically according to any method known by one having skill in the art.

It is contemplated that controller 2000 may be provided with a visual indicator in the form of lights, LEDs, symbology, etc. that provides a visual indication to the operator of the direction of rotation/pivoting of jaw portion 811*a* and/or when jaw portion 811*a* is centered or in a home position.

In operation, as first rotatable member 2100 is rotated, magnets 2120 supported thereon are moved relative to first Hall-Effect switch 2130 to actuate first Hall-Effect switch 2130, which in turn causes a circuit board (not shown) connected thereto to provide appropriate signals to drive components (e.g., a first drive shaft 1110*a*, as illustrated in FIG. 1A) of surgical device 800 to effectuate rotation of jaw portion 811*a*. Additionally, as second rotatable member 2200 is rotated, magnets 2220 supported thereon are moved relative to second Hall-Effect switch 2230 to actuate second Hall-Effect switch 2230, which in turn causes the circuit board (not shown) connected thereto to provide appropriate signals to drive components (e.g., a second drive shaft 1110*b*, as illustrated in FIG. 1A) of surgical device 800 to effectuate pivoting of jaw portion 811*a*.

Advantageously, rotation of first rotatable member 2100 in a first direction will effectuate rotation of jaw portion 811*a* in a first direction and rotation of first rotatable member 2100 in a second direction will effectuate rotation of jaw portion 811*a* in a second direction. Similarly, rotation of second rotatable member 2200 in a first direction will effectuate pivoting of jaw portion 811*a* in a first direction and rotation of second rotatable member 2200 in a second direction will effectuate pivoting of jaw portion 811*a* in a second direction.

As mentioned above, controller 2000 is configured to include a first rotatable member 2100 and a second rotatable member 2200, where second wheel 2200 may be positioned at least partially within first rotatable member 2100 and where second rotatable member 2200 may be oriented perpendicular with respect to first rotatable member 2100. Also, controller 2000 may include a first rotatable member 2100 and a second rotatable member 2200, where first rotatable member 2100 and second rotatable member 2200 may be permitted to be operated concurrently. However, it is contemplated that first rotatable member 2100 may be locked when second rotatable member 2200 is operated and vise versa.

Figure 4:
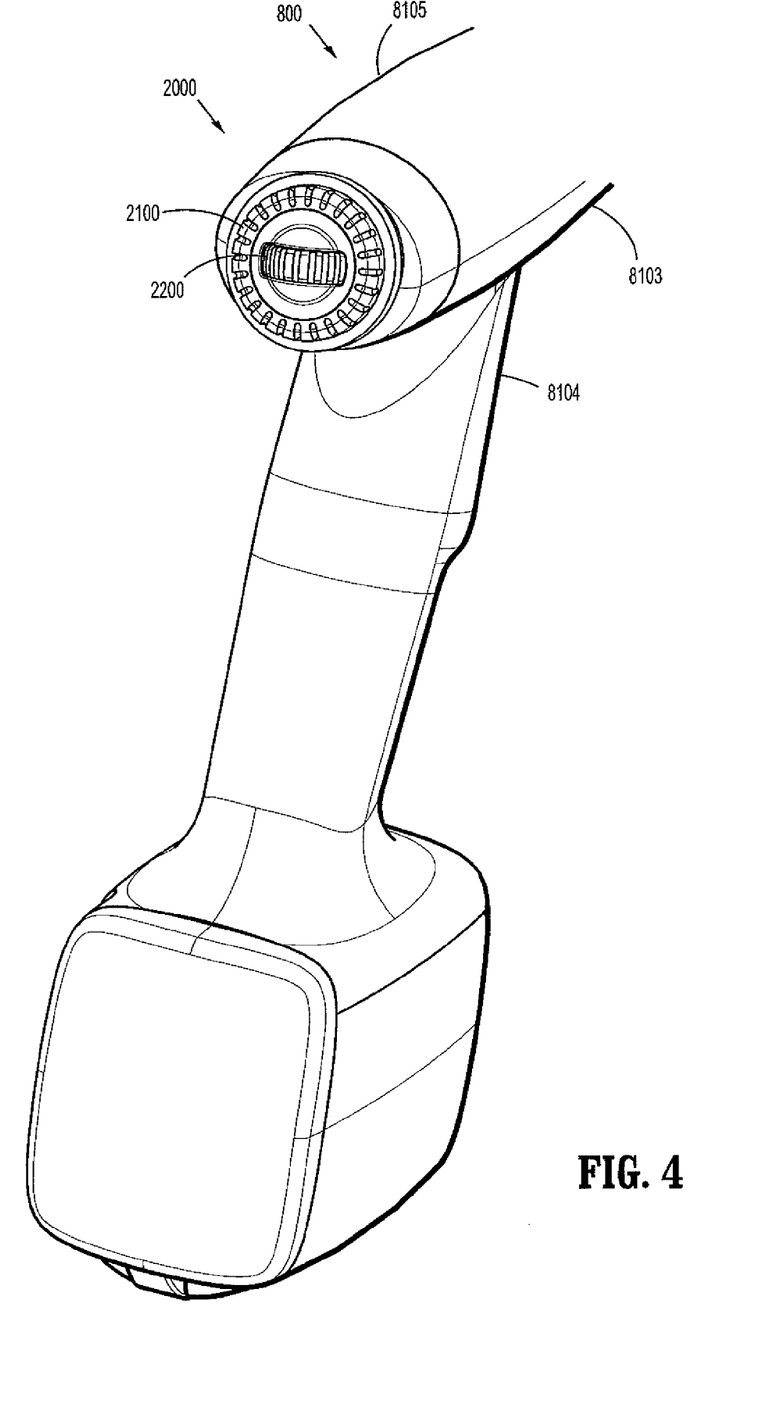
FIG. 4 is a perspective, rear view of a cab-forward style surgical device incorporating the controller, in accordance with the present disclosure.

Referring to FIG. 4, a perspective, rear view of a surgical device 800 incorporating controller 2000, in accordance with the present disclosure, is presented wherein the surgical device has a cab-forward style configuration. In particular, as described above with reference to FIG. 1B, surgical device includes an intermediate portion 8104 that is angled and extends proximally from upper portion 8105 of handle 8103.

From the foregoing and with reference to the various figure drawings, those skilled in the art will appreciate that certain modifications may also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical device, comprising:
   a handle;
   a shaft portion coupled to the handle, the shaft portion defining a shaft longitudinal axis;
   an end effector supported on a distal end of the shaft portion so as to rotate and pivot relative to the shaft portion;
   a first drive shaft extending through the shaft portion and operatively connected to the end effector;
   a second drive shaft extending through the shaft portion and operatively connected to the end effector; and
   a controller supported on the handle so as to be actuated by a thumb of a hand of an operator holding the handle with a single hand in a pistol-grip fashion, the controller including:
      a first rotatable member; and
      a second rotatable member;
      the first rotatable member being configured to rotate the first drive shaft in one of a first direction and a second direction upon a corresponding first direction and second direction rotation thereof to effectuate a corresponding first direction rotation and second direction rotation of the end effector relative to the shaft portion; and
      the second rotatable member being configured to rotate the second drive shaft in one of a first direction and a second direction upon a corresponding first direction and second direction rotation thereof to effectuate a corresponding first direction pivoting and second direction pivoting of the end effector relative to the shaft portion;
   wherein the controller includes:
   a first Hall-Effect switch associated with the first rotatable member for effectuating, the rotation of the first drive shaft; and
   a second Hall-Effect switch associated with the second rotatable member for effectuating the rotation of the second drive shaft.

2. The surgical device according to claim 1, wherein the first rotatable member defines an axis of rotation and the second rotatable member defines an axis of rotation; and wherein the axis of rotation of the second rotatable member is orthogonally oriented with respect to the axis of rotation of the first rotatable member.

3. The surgical device according to claim 1, wherein the first rotatable member defines an axis of rotation and the second rotatable member defines an axis of rotation.

4. The surgical device according to claim 1, wherein the first rotatable member and the second rotatable member are nested within one another.

5. The surgical device according to claim 1, further including a feedback mechanism for providing at least one of tactile and audible feedback relating to the rotational movement and the pivoting movement of the end effector.

6. The surgical device according to claim 5, wherein the feedback mechanism includes a leaf spring engaged with teeth provided on each of the first rotatable member and the second rotatable member.

7. The surgical device according to claim 1 wherein the end effector is pivotably connected to the distal end of the shaft portion so as to pivot in a single plane about a pivot axis extending orthogonal to the shaft longitudinal axis.

8. The surgical device according to claim 1, wherein a rate of rotation of the end effector is commensurate in scope with a rate of rotation of the first rotatable member, and wherein a rate of pivoting of the end effector is commensurate in scope with a rate of rotation of the second rotatable member.

9. The surgical device according to claim 1, wherein the handle includes:
   an upper portion supporting the shaft portion; and
   an intermediate portion extending from the upper portion, wherein the intermediate portion defines a longitudinal axis, and wherein the longitudinal axis of the intermediate portion is oriented at an angle of 30° relative to the shaft longitudinal axis.

10. The surgical device according to claim 1, wherein the end effector includes a acv portion.

11. A surgical device, comprising:
   a handle configured to be held by a hand of an operator in a pistol-grip fashion;
   a shaft portion extending from the handle, the shaft portion defining a shaft longitudinal axis;
   an end effector supported on a distal end of the shaft portion, the end effector being able to rotate and pivot relative to the shaft portion; and
   a controller supported on the handle so as to be actuated by a thumb of the hand of the operator holding the handle with a single hand, the controller including:
      a first rotatable member; and
      a second rotatable member;
      the first rotatable member being configured to rotate in one of a first direction and a second direction to effectuate a corresponding first direction rotation and second direction rotation of the end effector relative to the shaft portion; and
      the second rotatable member being configured to rotate in one of a first direction and a second direction to effectuate a corresponding first direction pivoting and second direction pivoting of the end effector relative to the shaft portion;
   wherein the controller includes:
   a first Hall-Effect switch associated with the first rotatable member for effectuating the rotation of the end effector; and
   a second Hall-Effect switch associated with the second rotatable member for effectuating the pivoting of the end effector.

12. The surgical device according to claim 11, wherein the first rotatable member defines an axis of rotation and the second rotatable member defines an axis of rotation.

13. The surgical device according to claim 11, wherein the end effector is pivotally connected to the distal end of the shaft portion so as to pivot in a single plane about a pivot axis extending orthogonal to the shaft longitudinal axis.

14. The surgical device according to claim 11 wherein a rate of rotation of the end effector is commensurate in scope with a rate of rotation of the first rotatable member, and wherein a rate of pivoting of the end effector is commensurate in scope with a rate of rotation of the second rotatable member.

15. A method of operating a surgical device, the method comprising the steps of:
   providing a surgical device including:
      a handle configured to be held by a hand of an operator in a pistol-grip fashion;
      a shaft portion extending from the handle, the shaft portion defining a shaft longitudinal axis;
      an end effector supported on a distal end of the shaft portion, the end effector being able to rotate and pivot relative to the shaft portion;
      a controller supported on the handle so as to be actuated by a thumb of the hand of the operator holding the handle with a single hand, the controller including;
      a first rotatable member; and
      a second rotatable member;
      the first rotatable member being configured to rotate in one of a first direction and a second direction to effectuate a corresponding first direction rotation and second direction rotation of the end effector relative to the shaft portion; and
      the second rotatable member being configured to rotate in one of a first direction and a second direction to effectuate a corresponding first direction pivoting and second direction pivoting of the end effector relative to the shaft portion;
   performing at least one of:
   rotating the first rotatable member to effectuate a rotation of the end effector relative to the shaft portion; and
   rotating the second rotatable member to effectuate a pivoting of the end effector relative to the shaft portion;
   wheren the controller includes:
   a first Hall-Effect switch associated with the first rotatable member for effectuating the rotation of the end effector; and
   a second Hall-Effect switch associated with the second rotatable member for effectuating the pivoting of the end effector.

* * * * *